(12) United States Patent
Schweitzer

(10) Patent No.: US 11,406,410 B2
(45) Date of Patent: Aug. 9, 2022

(54) SURGICAL INSTRUMENT HAVING A RELEASE MECHANISM FOR DECOUPLING A SHAFT SECTION FROM A HANDLE

(71) Applicant: Aesculap AG, Tuttlingen (DE)

(72) Inventor: Tom Schweitzer, Tuttlingen (DE)

(73) Assignee: AESCULAP AG, Tuttlingen (DE)

( * ) Notice: Subject to any disclaimer, the term of this patent is extended or adjusted under 35 U.S.C. 154(b) by 434 days.

(21) Appl. No.: 16/482,381

(22) PCT Filed: Feb. 2, 2018

(86) PCT No.: PCT/EP2018/052649
§ 371 (c)(1),
(2) Date: Jul. 31, 2019

(87) PCT Pub. No.: WO2018/141904
PCT Pub. Date: Aug. 9, 2018

(65) Prior Publication Data
US 2020/0000487 A1 Jan. 2, 2020

(30) Foreign Application Priority Data
Feb. 3, 2017 (DE) .......................... 102017102176.0

(51) Int. Cl.
*A61B 17/29* (2006.01)
*A61B 17/00* (2006.01)

(52) U.S. Cl.
CPC .. *A61B 17/2909* (2013.01); *A61B 2017/0046* (2013.01); *A61B 2017/292* (2013.01)

(58) Field of Classification Search
CPC .......... A61B 17/2909; A61B 2017/291; A61B 2017/2911; A61B 2017/2912; A61B 2017/2913; A61B 2017/2915; A61B 2017/2916; A61B 2017/2917; A61B 2017/2919; A61B 2017/292;
(Continued)

(56) References Cited

U.S. PATENT DOCUMENTS 5,507,297 A * 4/1996 Slater .................... A61B 17/29
600/564
2005/0125027 A1 6/2005 Knodel et al.
2012/0116395 A1 5/2012 Madan et al.
(Continued)

FOREIGN PATENT DOCUMENTS

DE 10357105 B3 4/2005
DE 102004030928 A1 2/2006
(Continued)

OTHER PUBLICATIONS

German Search Report for German Application No. 10 2017 102 176.0, with English translation, dated Dec. 5, 2017—21 pages.

*Primary Examiner* — Aaron F Roane
(74) *Attorney, Agent, or Firm* — Christopher A. Rothe; Culhane Meadows, PLLC

(57) ABSTRACT

A surgical instrument includes a shaft section connected to a handle that has a rigid handle part and a movable handle part. The surgical instrument also has a release mechanism that can be actuated such that the shaft section and the handle are decoupled from each other. The release mechanism has a preferably rocker-like actuating element that can be swiveled such that the shaft section and the handle are released from each other.

16 Claims, 1 Drawing Sheet

(58) Field of Classification Search
CPC .... A61B 2017/2922; A61B 2017/0046; A61B 2017/00464; A61B 2017/00469
USPC .......................................................... 606/1
See application file for complete search history.

(56) References Cited

U.S. PATENT DOCUMENTS

2013/0304041 A1   11/2013   Merz et al.
2016/0206337 A1   7/2016    Kärcher et al.

FOREIGN PATENT DOCUMENTS

| DE | 202008006005 U1 | 7/2008 |
|----|-----------------|--------|
| DE | 102011001891 A1 | 10/2012 |
| DE | 102012007650 A1 | 10/2013 |
| EP | 2510888 A1      | 10/2012 |
| EP | 2653120 A2      | 10/2013 |
| JP | 10118090 A      | 5/1998 |
| SU | 284247 A1       | 10/1970 |

* cited by examiner

SURGICAL INSTRUMENT HAVING A RELEASE MECHANISM FOR DECOUPLING A SHAFT SECTION FROM A HANDLE

CROSS REFERENCE TO RELATED APPLICATIONS

This application is the United States national phase entry of International Application No. PCT/EP2018/052649, filed Feb. 2, 2018, which claims the benefit of priority of German Application No. 10 2017 102 176.0, filed Feb. 3, 2017. The contents of International Application No. PCT/EP2018/052649 and German Application No. 10 2017 102 176.0 are incorporated by reference herein in their entireties.

FIELD

The present invention relates to a surgical instrument, such as a surgical grasping and/or cutting instrument, i.e. generally tubular shaft instruments. In addition to a shaft section, generic instruments have a handle consisting at least of a rigid part and a part which can be moved relatively to it.

BACKGROUND

Reusable surgical instruments, whether in minimally invasive surgery or endoscopy, are sterilized, disinfected or at least cleaned after each use. This process usually takes place in a central sterile supply facility (CSSD). In such CSSDs, a large number of different instruments are disinfected by differently qualified specialists.

Since surgical instruments have a high degree of compactness as a result of the optimization of installation space, it is necessary in most cases to dismantle/divide the instruments into their individual parts in order to guarantee complete disinfection. The mechanism responsible for disassembling the instruments into their individual parts is called the release mechanism. It must be ensured that this disassembling is as intuitive as possible, guarantees a high degree of reliability and, last but not least, can be executed efficiently in terms of time.

The German patent application DE 10 2012 007 650 A1 discloses a detachable mechanical coupling between a handle and a shaft to ensure that the individual components can be disassembled for a disinfection process. In this patent application, the components to be decoupled from each other rely on assuming a decoupling position in order to ensure disassembly.

The prior art generally discloses instruments in which return springs ensure that decoupling positions are taken. It should be noted, however, that these return springs depend on the position of the movable handle part relative to the rigid handle part.

A disadvantage of the prior art is that for a locking and unlocking modularly connectable component parts it must always be ensured that the individual parts are correctly positioned in relation to each other. If, for example, a user in a CSSD unintentionally restricts the free movability of a handle part, this can lead to incorrect disassembly/unlocking or to incorrect assembly/locking of the surgical instrument. In the worst case, this may result in a faulty surgical instrument, which can pose a health risk for patients, especially during intraoperative unlocking and locking processes.

SUMMARY

In view of this prior art, the present invention is based on the task of eliminating or at least mitigating the disadvantages arising from prior art and, in particular, of disclosing a surgical instrument whose release mechanism permits simpler assembly and disassembly of the instrument handle and shaft.

Furthermore, the invention aims to implement the release mechanism so as to be as intuitively as possible so that users are able to quickly disassemble and later assemble an instrument even without specific knowledge of the instrument in question.

The present invention also aims to provide a user who performs the assembly of handle and shaft section with an acoustic signal/feedback informing him of correct assembly.

This is achieved according to the invention by means of a surgical instrument described herein.

This design, according to the invention, of a surgical instrument offers further following advantages, for example:

The assembly/disassembly is carried out according to the invention (essentially) irrespectively of the handle position, resulting in a high degree of reliability as well as simpler assembly and disassembly.

A user, e.g. in a CSSD, can operate the release mechanism intuitively and does not have to observe any handle positions, which results in time savings in disinfection.

The suitability for use is increased in this way, as fewer criteria for correct disinfection have to be met.

The service life of the individual instruments is increased by the fact that less damage occurs due to incorrect (dis)assembly processes.

The release mechanism implements a Poka-Yoke principle, since both incorrect disassembly and incorrect assembly are not possible or only possible under the influence of force.

Compared to conventional solutions, no additional installation space is required since components already in use are employed.

Due to high modularity and similar parts, the solution can be implemented in an almost cost-neutral manner.

The object of invention is therefore a (minimally invasive) surgical instrument, such as a tubular shaft instrument, comprising a shaft section, which is connected at its proximal end section with an (instrument) handle, via which a gripping and/or cutting and/or holding function of the instrument can be realized/actuated. To this end, the handle has a rigid handle part (for holding the instrument) and a movable handle part (for actuating the instrument functions). In order to ensure the simple disassembly (and assembly) on which the invention is based, a release mechanism is also provided, which is designed in accordance with the invention such that upon its (manual, possibly singular) actuation the shaft section and the handle are decoupled/released from each other irrespectively of the current position of the movable handle part relative to the rigid handle part.

According to the invention, the release mechanism preferably has a (single) actuating element, which by means of a (single) actuating movement, e.g. pivoting motion, disengages/dismantles/unlocks/dismounts the shaft section, which has a rigid part and a push rod movable relative thereto, from the handle. Conversely, the actuating element also allows to plug the shaft section into the handle to ensure a blocking/assembling/mounting/locking after disinfection. Thus, the central idea of the invention is the fact that the release mechanism has an actuating element which, by means of an actuating movement, completely releases the shaft section, composed of a rigid part and a movable push rod, from the handle in distal direction. This means that there is no longer a snap connection between the shaft section and the handle, so that these components are freely movable by pulling the shaft section in distal direction (relative to the handle) and can therefore be completely decoupled from each other.

Stated in other words, the invention is distinguished in that the release mechanism has a (single) actuating element, which is shaped/constituted/designed such that the shaft section, composed of a rigid part and a movable push rod, and the handle are completely detachable from each other in distal direction.

In an advantageous embodiment, the swiveling movement of the (single) actuating element releases the shaft section and the handle from each other in distal direction irrespectively of the position of the movable handle part relative to the rigid handle part. This means that a user who dismantles the shaft section from the handle does not have to take any additional precautions to ensure its correctness. In particular, the position of the movable handle part relative to the rigid handle part is not to be taken into account. This results in a high level of operational safety not only during dismantling but also during assembly, which comes at the end of the disinfection cycle.

The actuating element is of preferably rocker-like design, i.e. configured in the manner of a seesaw. This means that is has proximal and distal sections which can be swiveled around a fulcrum. The rocker-like actuating element is referred to in the following, while the rocking-type motion is not absolutely necessary, but is merely a preferred embodiment. Thus, for example, it would also be possible to realize the actuating element as a pull or press button which, for example, is longitudinally displaceable in the rigid handle part and in the course of its actuating movement unlocks two locking/latching mechanisms in parallel fashion or serially, namely one for coupling the shaft section with the rigid handle part and the other one for coupling a motion transfer element in the shaft section with the movable handle part. It should be noted that such a pull or press button could also be replaced by a simple swivel lever, which unlocks the two locking/latching mechanisms during its swivel movement.

It is also advantageous if the swiveling movement of the actuating element releases both a first connection between the rigid handle part and the rigid part of the shaft section and a second connection between the movable handle part and the movable push rod of the shaft section in distal direction. During swiveling, an end section of the swiveled part is moved in one direction and the other end section is moved in the other direction. In the present case, the following effect is made use of: the part of the actuating element swiveled in the one direction releases a latching tab from the rigid part ("first connection"), the part of the actuating element swiveled in the other direction pushes a drive pin out of an eyelet/indentation ("second connection"), so that two connections are released by means of one swiveling movement, whereby the inventive double effect of the actuating element is efficiently achievable.

A further embodiment of the surgical instrument is distinguished in that the (single) swiveling movement of the preferably rocker-like actuating element simultaneously or successively in the course of this actuating movement/swiveling movement releases a first connection/coupling between the rigid handle part and a (rigid) part of the shaft section and a second connection between the movable handle part and a movable push rod (motion transfer element) of the shaft section. Thus, only one (single) movement of the preferably rocker-like actuating element is required to release both connections from each other, accelerating both the decoupling and locking process.

Furthermore, it is advantageous if the actuating element has an actuating surface pointing outwards (with respect to the handle/handle case), which causes the swiveling movement of the (rocker-like) actuating element via a preferably linear pushing motion and thus ensures the ability of the shaft section to get detached from the handle. Such a pushing motion, which compared to the height of the instrument only covers a very short distance, represents an intuitively understandable release mechanism even for inexperienced users. What is more, a linear and short pushing motion can be integrated into the system with low wear, which increases its service life.

A highly compact embodiment is preferably realized in that the actuating surface of the actuating element in a locked condition of handle and shaft section is essentially flush with an outer surface of the rigid handle part (handle case). Thus, the preferably rocker-like actuating element in the side view essentially has a triangular/wedge shape with a right angle, whose hypotenuse extends plane-parallel/complementary to/flush with the corresponding outside of the rigid handle part. The locked condition is defined as the state in which the actuating element assumes its initial position in a pretensioned state and couples/connects the handle with the shaft section such that the surgical instrument is ready for use. In order to enable a pushing motion/swiveling movement of the preferably rocker-like actuating element against the background of the flushness of the surfaces, a part of the rigid handle part is provided with a recess, which allows pressing the actuating surface and thus a swiveling movement of the preferably rocker-like actuating element.

It is also advantageous if the preferably rocker-like actuating element has a latching protrusion in its distal region, which protrusion in the case of the wedge shape of the actuating element forms an acute angle and is prepared/adapted to enter into a form fit with a receiving pocket of the shaft section in the locked condition. This form fit represents the first connection mentioned at the beginning. The contour of the latching protrusion can be designed variably and adapted to the installation space and force requirements. The form fit stands out due to its high robustness, which allows a reliable design of the release mechanism. The latching protrusion and its mating contour in the receiving pocket are to be manufactured as far as possible with low tolerances in axial direction in order to connect the shaft section to the handle without play.

In a further embodiment, the actuating element is pretensioned by a leaf spring formed by the rigid handle part. This ensures that the preferably rocker-like actuating element reliably connects the shaft section to the handle in the locked condition. The leaf spring is distinguished by its small required installation space and its economical production. Furthermore, the arrangement, according to the invention, of the leaf spring ensures a sufficiently large contact area between the actuating element and the leaf spring, which guarantees pretensioning over the entire service life. The leaf spring formed by the handle part can be realized both as an integral constituent part of the rigid handle part, but also as an additional component.

The movable handle part advantageously has a drive pin which is prepared/adapted to produce a form fit between the movable handle part and the push rod via an indentation in a push rod arranged at least partially within the shaft section in order to convert a rotation of the movable handle part into a translation of the push rod. This form fit represents the second connection mentioned at the beginning. The drive pin is pretensioned by a coil spring, for instance, in order to be in contact with the actuating element in every operating state. As soon as the pushing motion is exerted on the preferably rocker-like actuating element, it is ensured that the drive pin is released from the indentation of the push rod while maintaining the contact, thus decoupling the shaft section from the handle. According to the invention, the pushing motion of the actuating element leads to a detachability/dismantling ability of the instrument in every position of the movable handle part relative to the rigid handle part.

It is also advantageous if the preferably rocker-like actuating element has a contact surface that is prepared/adapted to be in contact with the drive pin such that it can be detached from the indentation irrespectively of the position/rotation of the movable handle part. The interaction between the preloaded drive pin and the contact surface, which in side view is long as compared to it, ensures that even if the movable handle part has just fully extended the push rod, there is still a contact which ensures the detachability of the handle from the shaft section by means of the pushing motion of the actuating part. The contact surface has a high surface smoothness in order to keep the friction between the drive pin and the contact surface low when the push rod is moved.

Especially when the latching protrusion of the preferably rocker-like actuating element engages in the receiving pocket of the shaft section such that with establishing the form fit an acoustic signal occurs by said snap-in process and signals a user the locked condition, the handling of the surgical instrument is intuitively and reliably made possible even for inexperienced users. The acoustic signal represents, for example, a click noise that occurs due to the latching protrusion snapping in place in the receiving pocket. Thus, the leaf spring biasing the actuating element causes the front side of the latching protrusion to strike the base of the receiving pocket such that the user perceives a clicking noise.

Another advantageous embodiment of the invention is distinguished in that the rocker-like actuating element is supported by a pivot axle which is connected to the rigid handle part and arranged on the side of the push rod facing away from the movable handle part. The pivot axle preferably extends so as to be offset to the centroid of a side surface of the actuating element in order to minimize the force to be applied for the pushing motion on the actuating element via the leverage effect. In this preferred case, the pivot axle ensures the rocking function/rocker-type design of the actuating element.

Further, it should also be pointed out that even those surgical instruments can be equipped with the release mechanism according to the invention which are operated by means of a rotating star. Here too, it is possible to release the connection between the fixed/rigid handle part and the shaft section as well as between the push rod and the movable handle part by means of a single actuating element. In such case, the locking is achieved via a spring-loaded collet connection instead of a form fit. By means of the actuating element which is axially movable in this exemplary embodiment, the handle and the shaft section are also decoupled here irrespectively of the handle position, i.e. the relative position between movable handle part and rigid handle part.

As can be seen from the above explanation of the present invention, a particularly preferred embodiment of the invention can be reduced to the following constructional principle:

Especially in the case of a rocker-like actuating element, it is well known that a pressure on the one end of the rocker makes this rocker end to be lowered or sink into a housing, for example, whereas the other end of the rocker is raised or emerges from the housing, for instance. The present invention makes use of this function by designing the likewise preferably rocker-like actuating element of the release mechanism according to the invention and positioning/supporting it on the rigid handle part (handle case) such that its one rocker end (to be pressed) presses directly or indirectly against a coupling element (drive pin) upon a press-type operation (enters the handle case), which coupling element presses the movable handle part (actuating lever/actuating knob/etc.) with a force/movement transfer component (push rod) within the instrument shaft, in order to thereby release this coupling (in concrete terms, the spring-loaded drive pin is thereby pressed out of the indentation/groove formed in the push rod), whereas the other rocker end, at which, preferably, e.g. a latching tab, a hook or eyelet is situated/formed which interacts with a corresponding undercut or projection on the instrument shaft, is pivoted from a position holding or locking the instrument shaft on the rigid handle part into a release position (then exits the handle housing), whereby the instrument shaft is released/can be detached from the handle.

In this way, one and the same actuating element of the release mechanism basically allows to decouple/unlock both the instrument shaft from the rigid handle part and the push rod mounted in the instrument shaft from the movable handle part in a single actuating movement, so that the instrument shaft together with the push rod mounted in it can be released/dismounted/removed from the handle. The assembly of the instrument shaft together with the push rod supported therein is done accordingly.

It is especially advantageous if the one actuating element has a double effect on the rigid part and the push rod. Consequently, the one actuating element serves as a double locking device.

In this embodiment, the actuating element firstly forms a latching tab situated at its distal end and projecting towards the rigid part; secondly, proximal to this latching tab, it forms a contact surface resting on a drive pin, whereby upon actuation of the actuating element the latching tab disengages from the rigid part and the contact surface partially slides off the drive pin. The actuating element is swiveled when actuated. The resulting upward movement of the distal end of the actuating element is used for leaving the form fit, as does the downward movement of the proximal end.

In other words, it can be said that the actuating element acts in two ways: First, it releases the form fit between the latching tab (of the actuating element) and the receiving pocket (of the rigid part) and secondly, it releases via the contact surface (of the actuating element) the form fit between the drive pin (of the movable handle part) and the indentation (of the push rod of the shaft section).

BRIEF DESCRIPTION OF THE DRAWING FIGURES

In the following, the invention is described in more detail using a preferred exemplary embodiment with reference to the accompanying Figures wherein.

The Figures are only schematic in nature and serve only to understand the invention. The same elements are provided with the same reference signs.

DETAILED DESCRIPTION

Figure 1:
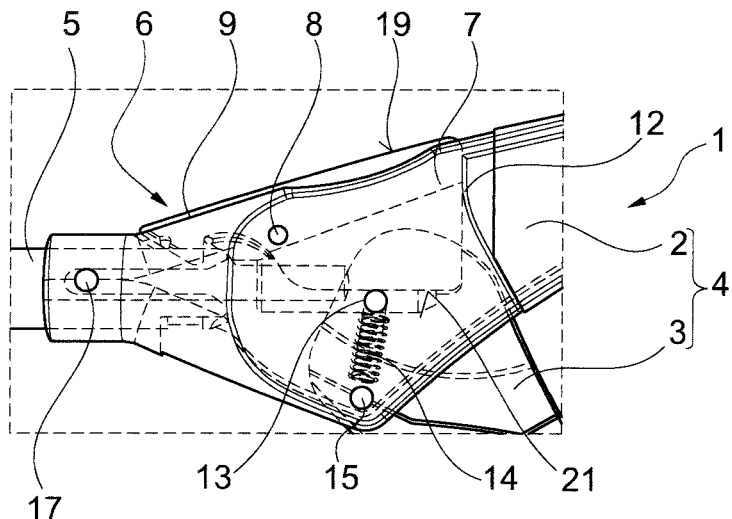
FIG. 1 shows a proximal end of a surgical instrument according to the invention in a locked condition.

FIG. 1 illustrates a proximal end of a surgical instrument 1. A shaft section/instrument shaft 5 consists, as explained in more detail in connection with FIG. 3, of a rigid or flexible part (tubular shell) 22 extending in the axial direction and a displaceable push rod 16 mounted therein. The shaft section 5 is connected at its proximal end section to an instrument handle 4. The latter has a rigid handle part (handle case) 2 and a handle part (actuation lever) 3 movable relative thereto.

The handle 4 and the shaft section 5 (together with the push rod supported therein) are mechanically coupled to each other via a release mechanism 6. The latter can be actuated such that the handle 4 and the shaft section 5 (together with the push rod mounted therein) can be decoupled from each other and separated. According to the invention, the release mechanism 6 features a rocker-like actuating element 7 for this purpose, which for its manual actuation is freely accessible from outside the rigid handle part 2. This actuating element can be pivoted/rotated around a pivot axle 8 mounted in the rigid handle part 2. The swiveling movement of the rocker-like actuating element 7 is caused by a pushing motion exerted by a user on an outwardly facing actuating surface 19 of the actuating element at its one rocker end.

Figure 3:
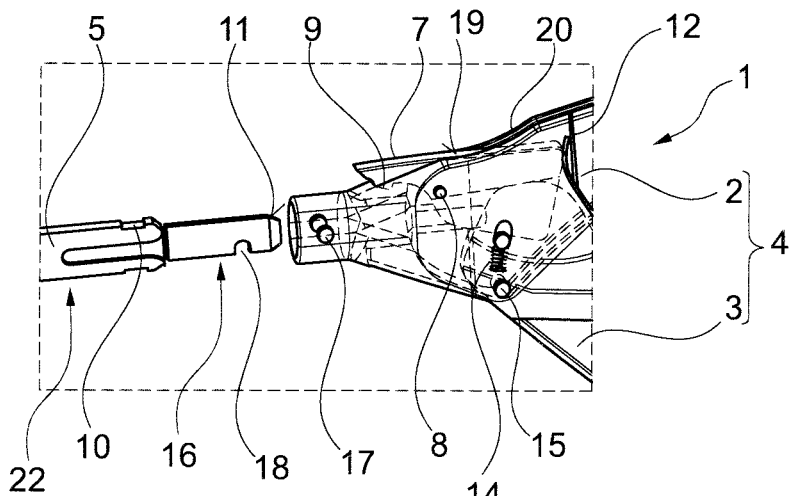
FIG. 3 shows a shaft section of the surgical instrument decoupled from a handle.

FIG. 1 shows the surgical instrument 1 in a locked condition. In this locked condition, the handle 4 and the shaft section 5 (together with the push rod mounted therein) are positively coupled to each other. This means that the tubular shell (instrument shaft) of the shaft section 5 is firmly connected to the rigid handle part 2, whereas the push rod 16 is operatively connected to the movable handle part 3 via a coupling mechanism or a coupling element. As soon as a user, such as an employee in a CSSD, actuates the actuating element 7 of the release mechanism for pivoting it, this causes two things:

For one thing, a first form fit between a latching protrusion 9 on the actuating element side and a receiving pocket/groove 10 on the shaft section side in the tubular shell of the shaft section 5, which is explained in more detail in FIG. 3, is released. This decouples the rigid handle part (handle case) 2 from the shaft section 5.

Secondly, at the same time or serially in the further course of the actuating movement of the actuating element 7, a second form fit between a drive pin (coupling element) 13 and an indentation/groove 18 in the push rod 16, also explained in more detail in connection with FIG. 3, will be released. This decouples the movable handle part 3 from the push rod 16 supported in the shaft section 5.

The rocker-like actuating element 7 can be manually actuated via its actuating surface 19 pointing outwards. In the side view shown in FIG. 1, this actuating surface is essentially flush with the outer surface of the rigid handle part 2 surrounding the actuating surface at the edge area. In addition, the actuating surface 19 is sufficiently spaced from a (not shown) grip surface of the rigid handle part (handle case) 2 and of the movable handle part 3 to keep the release mechanism 6, which can be triggered via the actuating element 7, in the locked state during use of the surgical instrument 1. Preferably, the actuating element is located on the side planned as the top of the rigid handle part, whereas the movable handle part 3 is located on the side planned as the bottom of the rigid handle part.

The rocker-like actuating element 7 is pretensioned by a leaf spring 12 resting on the rigid handle part in such a way that the locked condition prevails in an unactuated state (design position). The leaf spring 12 acts in the direction of the shaft section 5 and causes a torque on the actuating element toward the design position. The leaf spring 12 preferably has a convex curvature with respect to the actuating element 7. This causes a line contact between the leaf spring 12 and the actuating element 7 irrespectively of the bias by the leaf spring 12. The leaf spring 12 extends essentially transverse to the longitudinal direction of the rigid handle part 2 over its entire width.

The drive pin 13 is part of the movable handle part 3 or of a coupling mechanism (not shown) arranged downstream of it. When actuated, it is rotated about a rotation axle 15, which is part of the rigid handle part 2. Thus, it is supported so as to be able to be rotated relative to the rigid handle part 2, but cannot be shifted relative to it. The drive pin 13 is preloaded via a compression spring (coil spring) 14 toward the latching position. Furthermore, the drive pin 13 is mounted in an elongated hole, which is formed by the movable handle part 3. This elongated hole allows a relative movement between the drive pin 13 and the movable handle part 3.

If, for example, the movable handle part 3 is operated around the rotation axle 15, the drive pin 13 performs a movement in axial direction (corresponds to the longitudinal direction of the shaft section). Thus, the rotation of the movable handle part 3 is converted into a translation of the push rod 16 by means of the drive pin 13 mounted in the elongated hole. Due to the fact that the drive pin 13 is coupled with the indentation 18 in the push rod 16 via the second form fit, its movement is transferred to the push rod 16. This causes an operation of the surgical instrument 1. The release mechanism 6 remains unaffected.

In the present exemplary embodiment, the drive pin 13 is in direct contact with the rocker-like actuating element 7 via a contact surface 21. In the side view, the contact surface 21 extends parallel to the direction of movement of the push rod 16. This keeps the friction between the push rod and the contact surface of the actuating element to a minimum when the push rod 16 is actuated.

The first form fit, i.e. the form fit between the latching protrusion 9 and the receiving pocket 10, couples the shaft section 5 and the handle 4 (rigid handle part) in axial direction (longitudinal direction of the shaft section). A further form fit between the shaft section 5 and the rigid handle part 2 acts transverse to the axial direction. Thus, the shaft section 5 has a track (longitudinal groove/longitudinal slot) along its axial direction, into which a handle-side pin 17 engages in sliding manner. This pin is rigidly connected to the rigid handle part 2.

Figure 2:
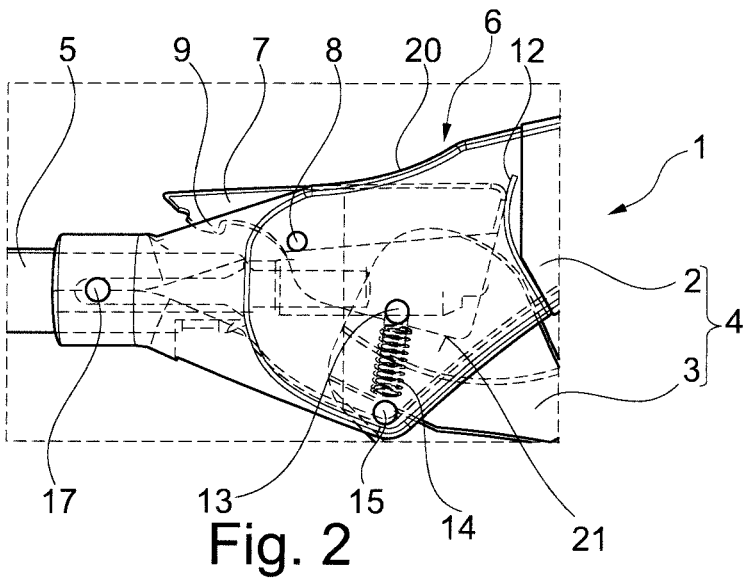
FIG. 2 shows the view from FIG. 1, with a swiveling movement of an actuating element having been induced.

FIG. 2 shows a second state, namely a swiveled state of the actuating element. In this swiveled state, a swiveling movement of the rocker-like actuating element 7 is brought about. By means of a pushing motion on the actuating surface 19, the actuating element thus rotates around the pivot axle 8. The pushing motion is made possible by a recess 20 in the rigid handle part 2. The swiveling movement causes a movement of the drive pin 13 in its elongated hole for disengaging the drive pin from the indentation/groove formed in the push rod. Thus, irrespectively of the position of the movable handle part 3 relative to the rigid handle part 2, a releasing of the second form fit is achieved, i.e. the form fit between the drive pin 13 and the indentation 18. The recess 20 is preferably designed with a concave curvature here. It has such a shape that it fits ergonomically to the shape of the thumb of a user.

At the same time, the latching protrusion 9 leaves the receiving pocket 10, decoupling the rigid part 22 of the shaft section 5 from the rigid handle part 2. During the pushing motion exerted on the actuating surface 19, the rocker-like actuating element 7 is pressed against the leaf spring 12. The force to be applied for a decoupling/dismantling the surgical instrument 1 can thus be controlled at least via the leaf spring 12.

All other components from FIG. 2 are already described on the basis of FIG. 1.

FIG. 3 shows a third state, namely a decoupled state. In this decoupled state, the shaft section 5 together with the push rod 16 mounted therein and the handle 4 are decoupled from each other and separated, so that a thorough disinfection of the individual components can be carried out.

In the decoupled state, the shape of the shaft section 5 is clearly visible. The push rod 16 proximally protrudes from the rigid part 22 of the shaft section 5. At the proximal tip of the push rod 16, an insertion chamfer 11 is shown, which allows a gentle insertion of the push rod 16 into handle 4, especially past the latching protrusion 19 of the actuating element 7. If the shaft section 5 is inserted into the handle again, i.e. if the surgical instrument is transferred from the decoupled state to the locked state, the actuating element 7, spring-loaded by the leaf spring 12, is deflected by the insertion slope 11 and the further profile of the push rod 16 before the latching protrusion 9 of the actuating element 7 snaps in place in the receiving pocket 10.

The first and the second form fit, i.e. the form fit between the latching protrusion 9 and the receiving pocket 10 as well as the form fit between the drive pin 13 and the indentation 18 are flexibly configurable in terms of their geometry. Due to the crenelated shape of the latching protrusion 9, it is advantageous if the receiving pocket 10 is essentially box-shaped. Due to the cylindrical shape of the drive pin 13, however, it is advantageous for an efficient second protrusion if the indentation 18 is curved.

All other components from FIG. 3 are already described on the basis of FIGS. 1 and 2.

The invention claimed is:
1. A surgical instrument comprising:
a shaft section;
a handle; and
a release mechanism,
a proximal end section of the shaft section being connected to the handle, and the release mechanism configured to actuate such that the shaft section and the handle are decoupled from each other,
the shaft section having a rigid, non-movable shaft part and a movable push rod, the handle having a first rigid, non-movable handle part and a second movable handle part which is movable relative to the first rigid, non-movable handle part,
the first, rigid, non-movable handle part connected to the rigid, non-movable shaft part via a first connection and the second movable handle part is connected to the movable push rod via a second connection, and
the release mechanism comprising an actuating part which, by means of one single swiveling movement of the actuating part, completely and directly releases both the first connection and the second connection and thus the shaft section and the handle from one another in a distal direction so that the shaft section and the handle are freely movable by pulling the shaft section into the distal direction relative to the handle.

2. The surgical instrument according to claim 1, wherein the swiveling movement of the actuating part causes the shaft section and the handle to be completely released in the distal direction irrespectively of the position of the second movable handle part relative to the first rigid, non-movable handle part.

3. The surgical instrument according to claim 1, wherein the actuating part is a rocker.

4. The surgical instrument according to claim 1, wherein the actuating part comprises an outwardly facing actuating surface, which is directly accessible for a user and thus positioned to be directly pushed by the user, and which brings about the swiveling movement of the actuating part via a pushing motion and in this way ensures that the shaft section is releasable from the handle.

5. The surgical instrument according to claim 4, wherein the actuating surface extends so as to be flush with an outer surface of the first rigid, non-movable handle part in a locked condition of the handle and the shaft section.

6. The surgical instrument according to claim 5, wherein the actuating part comprises a latching protrusion that establishes a form fit with a receiving pocket of the rigid, non-movable shaft part in the locked condition.

7. The surgical instrument according to claim 6, wherein the actuating part in the locked condition is pre-tensioned by a leaf spring formed by the first rigid, non-movable handle part.

8. The surgical instrument according to claim 6, wherein the latching protrusion engages in the receiving pocket such that upon occurrence of the form fit an acoustic signal is produced as a result of a snap-in process, which signals the locked condition to a user.

9. The surgical instrument according to claim 1, wherein the second movable handle part comprises a drive pin that establishes a form fit between the second movable handle part and the push rod via an indentation in the push rod, in order to transfer a rotation of the second movable handle part into a translation of the push rod.

10. The surgical instrument according to claim 9, wherein the actuating part has a contact surface configured to contact the drive pin in such a manner that the drive pin is releasable from the indentation irrespectively of the position of the movable handle part.

11. The surgical instrument according to claim 1, wherein the actuating part has a double effect on the rigid, non-movable shaft part and the movable push rod.

12. The surgical instrument according to claim 11, wherein the actuating part has its distal end provided with a latching tab projecting toward the rigid, non-movable shaft part and proximal thereto a contact surface resting on a drive pin, wherein, upon actuation of the actuating part, the latching tab is disengaged from the rigid, non-movable shaft part and the contact surface partially slides along the drive pin.

13. The surgical instrument according to claim 1, wherein the first connection between the first rigid, non-movable handle part and the rigid, non-movable shaft part is established by a latching protrusion of the actuating part being in a form fit engagement with a receiving pocket of the rigid, non-movable shaft part.

14. The surgical instrument according to claim 13, wherein the second connection between the second movable handle part and the movable push rod is established by a drive pin of the second movable handle part being in a form fit engagement with an indentation provided in the movable push rod.

15. The surgical instrument according to claim 14, wherein the release mechanism is configured such that when the actuating part is swiveled by a user, the latching protrusion of the actuating part is disengaged from the receiving pocket of the rigid, non-movable shaft part and a contact surface of the actuating part pushes the drive pin of the second movable handle part out of the indentation of the movable push rod.

16. The surgical instrument according to claim 15, wherein the actuating part has an actuating surface which faces outwardly and which is directly accessible for a user and thus can be directly pushed by the user in order to initiate the swiveling movement of the actuating part.

* * * * *